(12) United States Patent
Hojeibane

(10) Patent No.: US 6,238,409 B1
(45) Date of Patent: May 29, 2001

(54) ARTICULATED EXPANDABLE INTRALUMINAL STENT

(75) Inventor: Hikmat Hojeibane, Franklin Park, NJ (US)

(73) Assignee: JOhnson & Johnson Interventional Systems Co., Miami Lakes, FL (US)

(*) Notice: Subject to any disclaimer, the term of this patent is extended or adjusted under 35 U.S.C. 154(b) by 0 days.

(21) Appl. No.: 09/296,060

(22) Filed: Apr. 21, 1999

Related U.S. Application Data (63) Continuation of application No. 08/814,182, filed on Mar. 10, 1997, now Pat. No. 5,911,732.

(51) Int. Cl.⁷ .................................................. A61M 29/00
(52) U.S. Cl. ........................................ 606/194; 623/1.16
(58) Field of Search .............................. 606/194, 198, 606/191, 192, 195; 623/1, 12, 1.16, 1.22, 1.12

(56) References Cited

U.S. PATENT DOCUMENTS

| | | | | |
|---|---|---|---|---|
| 3,657,744 | | 4/1972 | Ersek | 3/1 |
| 4,503,569 | | 3/1985 | Dotter | 3/1.4 |
| 4,553,545 | | 11/1985 | Maass et al. | 128/341 |
| 4,580,568 | | 4/1986 | Gianturco | 128/345 |
| 4,681,110 | | 7/1987 | Wiktor | 128/343 |
| 4,733,665 | | 3/1988 | Palmaz | 128/343 |
| 4,776,337 | | 10/1988 | Palmaz | 128/343 |
| 4,795,458 | | 1/1989 | Regan | 623/1 |
| 4,886,062 | | 12/1989 | Wiktor | 128/343 |
| 5,102,417 | | 4/1992 | Palmaz | 606/195 |
| 5,104,404 | | 4/1992 | Wolff | 623/1 |
| 5,133,732 | | 7/1992 | Wiktor | 606/195 |
| 5,135,536 | * | 8/1992 | Hillstead | 606/195 |
| 5,192,307 | | 3/1993 | Wall | 623/1 |
| 5,195,984 | * | 3/1993 | Schatz | 606/194 |
| 5,266,073 | | 11/1993 | Wall | 623/1 |
| 5,269,802 | | 12/1993 | Garber | 606/191 |
| 5,290,305 | | 3/1994 | Inoue | 606/191 |
| 5,316,023 | * | 5/1994 | Palmaz et al. | 606/198 |
| 5,383,892 | * | 1/1995 | Cardon et al. | 623/1.16 |
| 5,421,955 | | 6/1995 | Lau et al. | 216/48 |
| 5,443,498 | | 8/1995 | Fontaine | 623/1 |
| 5,443,500 | | 8/1995 | Sigwart | 623/1 |
| 5,449,373 | * | 9/1995 | Pinchasik et al. | 623/1.22 |
| 5,496,365 | | 3/1996 | Sgro | 623/1 |
| 5,514,154 | | 5/1996 | Lau et al. | 606/195 |
| 5,527,354 | | 6/1996 | Fontaine et al. | 623/1 |
| 5,569,295 | | 10/1996 | Lam | 606/198 |
| 5,591,197 | | 1/1997 | Orth et al. | 606/198 |
| 5,593,442 | | 1/1997 | Klein | 623/12 |
| 5,603,721 | | 2/1997 | Lau et al. | 606/195 |
| 5,607,442 | | 3/1997 | Fischell et al. | 606/191 |
| 5,643,312 | | 7/1997 | Fischell et al. | 606/198 |
| 5,669,936 | | 9/1997 | Lazarus | 623/1 |
| 5,733,303 | | 3/1998 | Israel et al. | 606/198 |
| 5,807,404 | | 9/1998 | Richter | 623/1 |
| 5,836,964 | | 11/1998 | Richter et al. | 606/194 |

FOREIGN PATENT DOCUMENTS

| | | | | |
|---|---|---|---|---|
| 296 15 969 U1 | 12/1996 | (DE) | | A61F/2/04 |
| 0 566 807 A1 | 10/1993 | (EP) | | A61F/2/06 |
| 0 662 307 A1 | 7/1995 | (EP) | | A61F/2/06 |

\* cited by examiner

*Primary Examiner*—Kevin Truong
(74) *Attorney, Agent, or Firm*—Paul A. Coletti

(57) ABSTRACT

The present invention includes: an expandable, tubular shaped prosthesis having first and second ends and a wall surface disposed between the first and second ends, the wall surface being formed by a plurality of intersecting elongate members; and a catheter, having an expandable, inflatable portion associated therewith and including means for mounting and retaining the expandable tubular shaped prosthesis on the expandable, inflatable portion, whereby upon inflation of the expandable, inflatable portion of the catheter, the prosthesis is formed radially outwardly into contact with the body passageway. The articulation in the form of a rounded wire frame loop connects similar stent bodies. Also, rounded open connectors and shortened cells in the stent allow for greater flexibility.

18 Claims, 6 Drawing Sheets

ARTICULATED EXPANDABLE INTRALUMINAL STENT

This application is a continuation of Ser. No. 08/814,182 filed Mar. 10, 1997, U.S. Pat. No. 5,911,732.

FIELD OF THE INVENTION

The invention relates to an expandable intraluminal stent for use within a body passageway or duct and, more particularly, improved, flexible, expandable intraluminal vascular stents which are particularly useful for repairing blood vessels narrowed or occluded by disease; and a method and apparatus for implanting expandable intraluminal stents.

BACKGROUND OF THE INVENTION

Intraluminal endovascular grafting ("stenting") has been demonstrated by experimentation to present a possible alternative to convention vascular surgery. Intraluminal endovascular grafting involves the percutaneous insertion into a blood vessel of a tubular prosthetic graft and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular stents have included coiled stainless steel springs; helically would coil springs manufactured from an expandable heat-sensitive material; and expanding stainless steel stents formed of stainless steel wire in a zig-zag pattern. In general, the foregoing structures have one major disadvantage in common. Insofar as these structures must be delivered to the desired location within a given body passageway in a collapsed state, in order to pass through the body passageway, there is no effective control over the final, expanded configuration of each structure. For example, the expansion of a particular coiled spring-type graft or "stent" is predetermined by the spring constant and modulus of elasticity of the particular material utilized to manufacture the coiled spring structure. These same factors predetermine the amount of expansion of collapsed stents formed of stainless steel wire in a zig-zag pattern. In the case of intraluminal grafts, or prostheses, formed of a heat sensitive material which expand upon heating, the amount of expansion is likewise predetermined by the heat expansion characteristics of the particular alloy utilized in the manufacture of the intraluminal grafts.

Thus, once the foregoing types of intraluminal "stents" are expanded at the desired location within a body passageway, such as within an artery or vein, the expanded size of the stent cannot be changed. If the diameter of the desired body passageway has been miscalculated, an undersized stent might not expand enough to contact the interior surface of the body passageway, so as to be secured thereto. It may then migrate away from the desired location within the body passageway.

Another alternative to conventional vascular surgery has been percutaneous balloon dilation of elastic vascular stenoses, or blockages, through use of a catheter mounted angioplasty balloon. In this procedure, the angioplasty balloon is inflated within the stenosed vessel, or body passageway, in order to shear and disrupt the wall components of the vessel to obtain an enlarged lumen. With respect to arterial atherosclerotic lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Although the balloon dilation procedure is typically conducted in the catheterization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as the left main coronary artery, which leads into the heart. If an intimal flap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

This invention relates to intraluminal stent implants for maintaining patency of a body lumen in humans and animals and especially to such implants for use in blood vessels. The present invention comprises an improvement to balloon expandable stents which are generally cylindrical in shape and have a plurality of metal elements joined to permit flexing of the cylindrical body along the longitudinal axis of the body, whereby the stent can conform to a curved body lumen. One such stent has metal elements made up of wire loops in a wound structure which allows individual loops to move with respect to one another. When a stent with this structure is expanded in a body lumen, the winding can follow curves in the body lumen. Typical of the articulation used to join stents are the stents disclosed in U.S. Pat. Nos. 4,733,665 and 4,776,337 issued to Palmaz which are incorporated herein by reference.

Another such stent is a Wiktor-type (Medtronic, Inc.) stent improved by having metal elements made up of individual stent segments joined together by flexible members such that the members will allow the stent segments to adapt to curved body lumen. Such stents can be deployed in a body lumen by means appropriate to their design. For example, in the case of the Wiktor-type stent, it can be fitted over the inflatable element of a balloon catheter and expanded by the balloon to force the stent into contact with the body lumen. Or, for example, in the case of the Palmaz and Palmaz-Schatz (Johnson & Johnson Interventional Systems) stents, can be mounted onto a catheter which holds the stent as it is delivered through the body lumen and then releases the stent and allows it to expand into contact with the body lumen. This deployment is effected after the stent has been introduced percutaneously, transported transluminally and positioned at a desired location by means of the catheter.

An important use of these stents is found in situations where part of the vessel wall or stenotic plaque blocks or occludes blood flow in the vessel. Dilation of the blood vessel is usually undertaken to correct a blood vessel occlusion i.e., a balloon catheter is utilized in a PTCA procedure to enlarge the occluded portion of the blood vessel. However, the dilation of the occlusion can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Moreover, such metal stents with good longitudinal flexibility can conform readily to vessels having curves and irregularities. However, such stents have limited ability to provide effective patching of perforated vessels due to the spacing between metal elements. Also, such metal stents also have limited ability to carry and deliver drugs, such as anti-restenois drugs or anti-coagulant drugs, to the site of an intravascular injury.

Accordingly, prior to the development of the actual stents such as those cited above, there has been no expandable intraluminal vascular stent, and method and apparatus for expanding the lumen of a body passageway, which: prevents recurrence of stenoses in the body passageway; can be flexibly utilized for critical body passageways, such as the left main coronary artery of a patient's heart; prevents recoil of the body passageway wall; and allows the intraluminal graft to be expanded to a variable size to prevent migration of the graft away from the desired location; and to prevent rupturing of the body passageway by the expanded graft. Therefore, the art has sought an expandable intraluminal vascular graft, and method and apparatus for expanding the lumen of a body passageway which: prevents recurrence of stenoses in the body passageway; is believed to be able to be utilized in critical body passageways, such as the left main coronary artery of the heart; prevents recoil of the body passageway; and can be expanded to a variable size within the body passageway to prevent migration of the graft away from the desired location; and to prevent rupturing of the body passageway by the expanded graft.

SUMMARY OF THE INVENTION

In accordance with the invention the foregoing advantages have been achieved through the present expandable intraluminal vascular stent. The present invention includes tubular shaped members having first and second ends and a wall surface disposed between the first and second ends, the wall surface being formed by a plurality of intersecting elongate members, at least some of the elongate members intersecting with one another intermediate the first and second ends of the tubular shaped member; the tubular shaped member having a first diameter which permits intraluminal delivery of the tubular shaped member into a body passageway having a lumen; and the tubular shaped member having a second, expanded diameter, upon the application from the interior of the tubular shaped member of a radially, outwardly extending force, which second diameter is variable and dependent upon the amount of force applied to the tubular shaped member, whereby the tubular shaped member may be expanded to expand the lumen of the body passageway.

The stents are connected by (1) a spiral loop structure; or (2) a semi-detached sinusoidal connector that is generally perpendicular to the longitudinal axis of the stent which allows greater flexibility in the body lumen, in either event causing the stent to be particularly adapted to articulate in the body.

In accordance with the invention, the foregoing advantages have also been achieved through the present method for expanding the lumen of a body passageway. The method of the present invention comprises the steps of: inserting an intraluminal graft, disposed upon a catheter, into the body passageway until it is disposed adjacent a desired location within the body passageway; and expanding a portion of the catheter to cause the intraluminal graft to radially expand outwardly into contact with the body passageway until the lumen of the body passageway at the desired location of the body passageway has been expanded, whereby the intraluminal graft prevents the body passageway from collapsing and decreasing the size of the expanded lumen.

In accordance with the invention, the foregoing advantages have also been achieved through the present apparatus for intraluminally reinforcing a body passageway. The present invention includes: an expandable, tubular shaped prosthesis having first and second ends and a wall surface disposed between the first and second ends, the wall surface being formed by a plurality of intersecting elongate members; and can be used in combination with a catheter, having an expandable, inflatable portion associated therewith and including means for mounting and retaining the expandable tubular shaped prosthesis on the expandable, inflatable portion, whereby upon inflation of the expandable, inflatable portion of the catheter, the prosthesis is formed radially outwardly into contact with the body passageway. The articulation in the form of a rounded wire frame loop or a semi-detached sinusoidal connector that is generally perpendicular to the longitudinal axis of the stent connects similar stent bodies. Also, rounded connectors and shortened cells in the stent allow for greater flexibility.

The expandable intraluminal vascular stent, method for expanding the lumen of a body passageway, and apparatus for intraluminally reinforcing a body passageway of the present invention, when compared with previously proposed prior art intraluminal stents, methods for implanting them, and balloon dilation techniques have the advantage of: preventing recurrence of stenoses; is believed to permit implantation of stents in critical body passageways, such as in the left main coronary artery of the heart; prevents recoil of the body passageway; and permits expansion of the graft to a variable size dependent upon conditions within the body passageway, and dependent on the location of articulation of the stent.

DETAILED DESCRIPTION OF THE INVENTION

In FIGS. 1–6 stents, that is expandable prostheses for a body passageway, are illustrated. It should be understood that the terms "stents" and "prostheses" are interchangeably used to some extent in describing the present invention, insofar as the method, apparatus, and structures of the present invention may be utilized not only in connection with an expandable intraluminal vascular graft for expanding partially occluded segments of a blood vessel, or body passageways, but may also be utilized for many other purposes as an expandable prosthesis for many other type of body passageways. For example, expandable prostheses may also be used for such purposes as: (1) supportive graft placement within blocked arteries opened by transluminal recanalization, but which are likely to collapse in the absence of an internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the urethra; and (5) supportive graft reinforcement of reopened and previously obstructed bile ducts. Accordingly, use and the term "prosthesis" encompasses the foregoing usage's within various types of body passageways, and the use of the term "intraluminal graft" encompasses use for expanding the lumen of a body passageway. Further, in this regard, the term "body passageway" encompasses and duct within the human body, such as those previously described, as well as any vein, artery, or blood vessel within the human vascular system.

Figure 1:
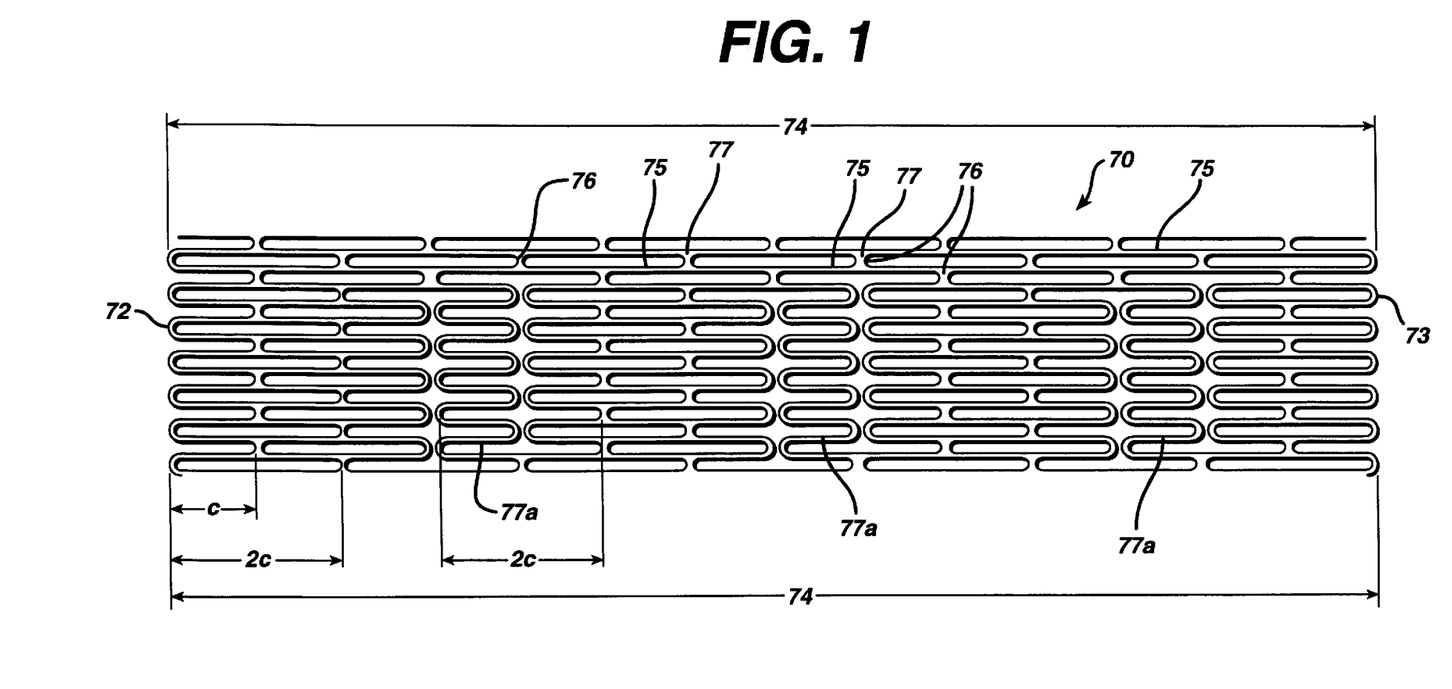
FIG. 1 is a plan view of a stent of this invention.
Figure 4:
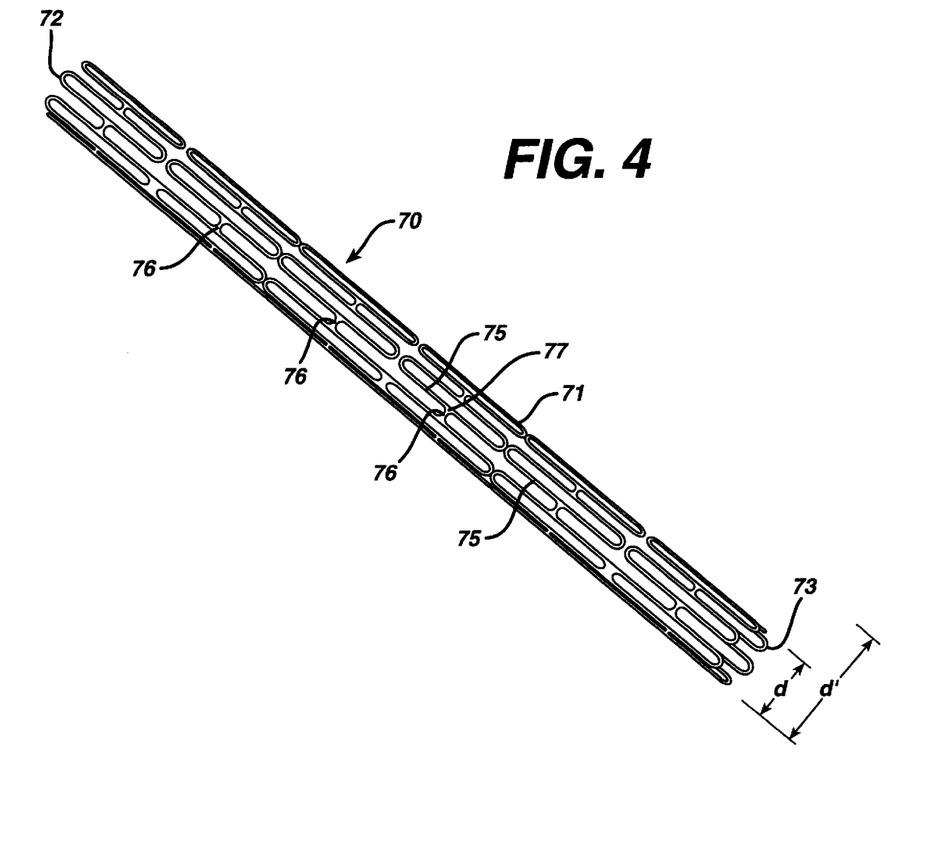
FIG. 4 is a perspective view of the stent of FIG. 1.

With reference to FIGS. 1 and 4, the expandable intraluminal vascular graft, or prosthesis, 70 is shown to generally comprise a tubular shaped member 71 having first and second ends 72, 73 and a wall surface 74 disposed between the first and second end 72, 73. Preferably, the wall surface 74 is formed by a plurality of intersecting elongate members 75, 76 with at least some of the elongate members 75, 76 intersecting with one another intermediate the first and second ends 72, 73 of the tubular shaped member 71, such as shown at intersection points 77. Tubular shaped member 71 has a first diameter, d, which to be hereinafter described in greater detail, permits intraluminal delivery of the tubular shaped member 71 into a body passageway 70 having a lumen already well known in the art. Upon the application from the interior of the tubular shaped member 71 of a radially, outwardly extending force, to be hereinafter described in greater detail tubular shaped member 71 has a second, expanded diameter, d', which second diameter d' is variable in size and dependent upon the amount of force applied to the tubular shaped member 71.

Elongate members 75, 76, which form wall surface 74 of tubular shaped member 71, may be any suitable material which is compatible with the human body and the bodily fluids (not shown) with which the vascular graft, or prosthesis, 70 may come into contact. Elongate members 75, 76 must also be made of a material which has the requisite strength and elasticity characteristics to permit the tubular shaped member 71 to be expanded from the configuration shown in FIG. 1 to the expanded configuration and further to permit the tubular shaped member 71 to retain its expanded configuration with an enlarged diameter d'. Suitable materials for the fabrication of tubular shaped member 71 would include silver, tantalum, stainless steel, gold, titanium or any suitable plastic material having the requisite characteristics previously described. Preferably, elongate members 75, 76 are fabricated from 316L stainless steel. Preferably, the elongate members 75, 76 illustrated are small diameter stainless steel wires having a cylindrical cross-section. It should of course be understood that each elongate member 75, 76 could have other cross-sectional configurations, such as triangular, square, rectangular, hexagonal, etc. Further, it is preferable that the plurality of elongate members 75, 76 are fixedly secure to one another where the elongate members 75, 76 intersect with one another, such as at the intersection points 77. Elongate members 75, 76 could be fixedly secured to one another in any conventional manner, such as by welding, soldering, or gluing, such as with a suitable epoxy glue; however, it is preferred that the intersection points 77 are one continuous piece. By fixedly securing the elongate members 75, 76, to one another, tubular member 71 is provided with a relatively high resistance to radial collapse, and the tubular shaped member 71 has the ability to retain its enlarged diameter, d'.

When fabricating tubular shaped member 71, it can be initially fabricated in the configuration shown in FIG. 1 with diameter, d. Alternatively, it can be fabricated with a diameter which is larger than initial diameter d and after fabrication, tubular shaped member 71 could be carefully collapsed to have diameter d shown in FIG. 1. During the collapsing of tubular shaped member 71, care must be taken to insure that overlapping of adjacent elongate member 75, 76 is avoided.

Strategically placed about the circumference of the prosthesis 70 are curved connectors 77a, which, intact, for the predominate parts of the stent 70. These connectors shorten the length of the "rectangles" 77, 75, 76, 77, and thus enhance the flexibility of the stent 70. This occurs because the closed "rectangles" 77, 75, 76, 77 can be as small as one cell length (c) along the length of the slots, as compared with the two cell length (2c) seen in certain open "rectangles" 77, 75, 76, 77a. The ratio of the open to closed rectangles can be as low as just greater than 1:1 to as high as 5:1 depending on flexibility desired. Most desirably, it has been found that one is able to use a flexibility ratio from about 1.5 to about 3.0. That is, an "open" cell length is anywhere 1½ and 3 times any "closed" cell length. The slots (c) themselves are found to be useful at no larger than 1.5 cm length. Moreover, the new "rectangles" have an open side, creating even greater flexibility. The entire length of a stent can range from about 3 cm for a coronary stent to about 18 cm for an aortic stent, with a wall thickness between 0.0025" and 0.008".

It has been found that it is useful to have the open cells spaced longitudinally as well as radially along the stent. Yet, it has further been found that these connectors do not have to be symmetrically spaced. In fact, it is believed in order to better induce bending in a certain given direction, it would be useful to have certain open areas concentrated on one side of the stent. These open areas will allow bending in the direction of the open areas. This bending will thereafter be more likely in that given direction.

Figure 2:
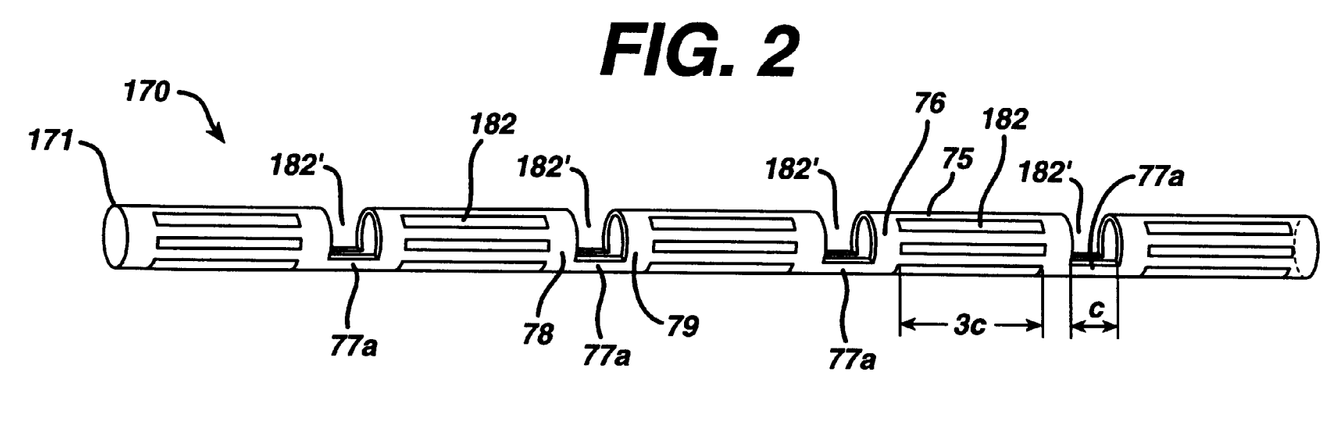
FIG. 2 is a schematic view of an alternate embodiment stent of this invention.
Figure 5:
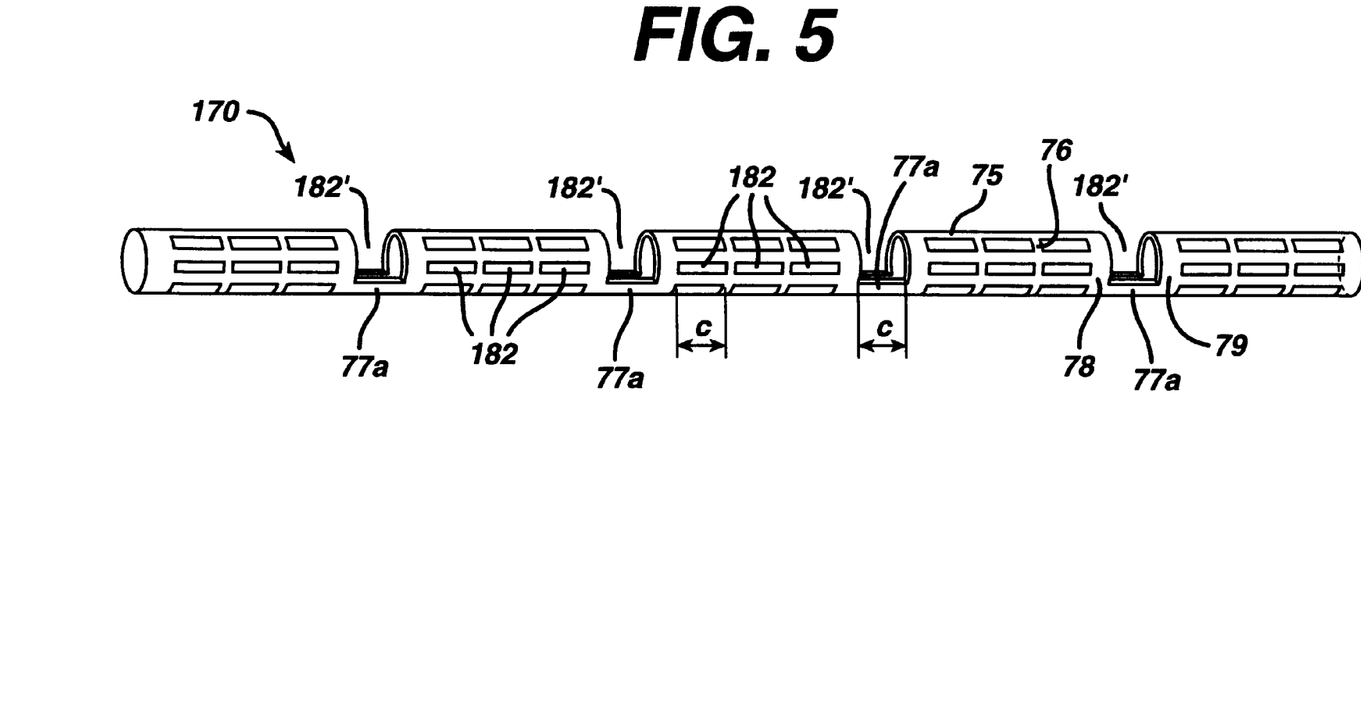
FIG. 5 is a schematic view of the stent of FIG. 2.

With reference now to FIGS. 2 and 5, other embodiments of expandable intraluminal vascular graft, or prosthesis, 170, 170' are analogized. The intraluminal vascular graft, or prosthesis, 170 of FIGS. 2 and 5 will have a plurality of elongate members 75, 76 formed by a plurality of thin bars 78, 79 which are preferably fixedly secured to one another in a closed perimeter cell where the bars 78, 79 intersect with one another. Similar to the stent of FIGS. 1 and 4. Further, there are contained a plurality of curved connectors 77a which help form openings 182 all along the stent. These bars preferably have a thin, rectangular cross-sectional configuration, and may be joined to one another in any conventional manner, such as by welding, braising, soldering, or may be formed integral with one another from polymers, conventional metal such as steel, or memory metals (e.g. nitinol), although preferentially, the stent 170 is formed from one piece. Most preferably, tubular shaped member 171 is initially a thin-walled stainless steel tube, and the openings 182 between the intersecting bars and are formed by a conventional etching process, such as electro-mechanical or laser etching, whereby the resultant structure is a tubular shaped member 171 having a plurality of intersecting elongate members 75, 76. The embodiment of graft, or prosthesis, 170 of FIG. 2, likewise can assume an expanded configuration as previously described in connection with FIG. 1, upon the application from the interior of the tubular shaped member 171 of a radially, outwardly extending force. It should be further understood that the embodiment of vascular graft, or prosthesis, 170 of FIG. 2, could also be generally described as a balloon expandable stent.

In FIG. 2, it is seen that the length of openings 182 are 3 times the length of openings 182. In FIG. 5, the openings 182 are equal to the length of the openings 182'. Yet, with flexible connectors 77a, the stent 170' of FIG. 5 will also be flexible, like the stent 170 of FIG. 2.

The stent 270 of the third particular embodiment (FIGS. 3) contains a spiral connector "S" between a series of cell type stents 271, 272. These spiral connectors are able to be formed such that they may be either linear or wave-like in shape. The final shape of this connector will depend primarily upon the desire of the user to have greater or lesser flexibility in the area of the articulation between the stents as the spiral connector.

Figure 3:
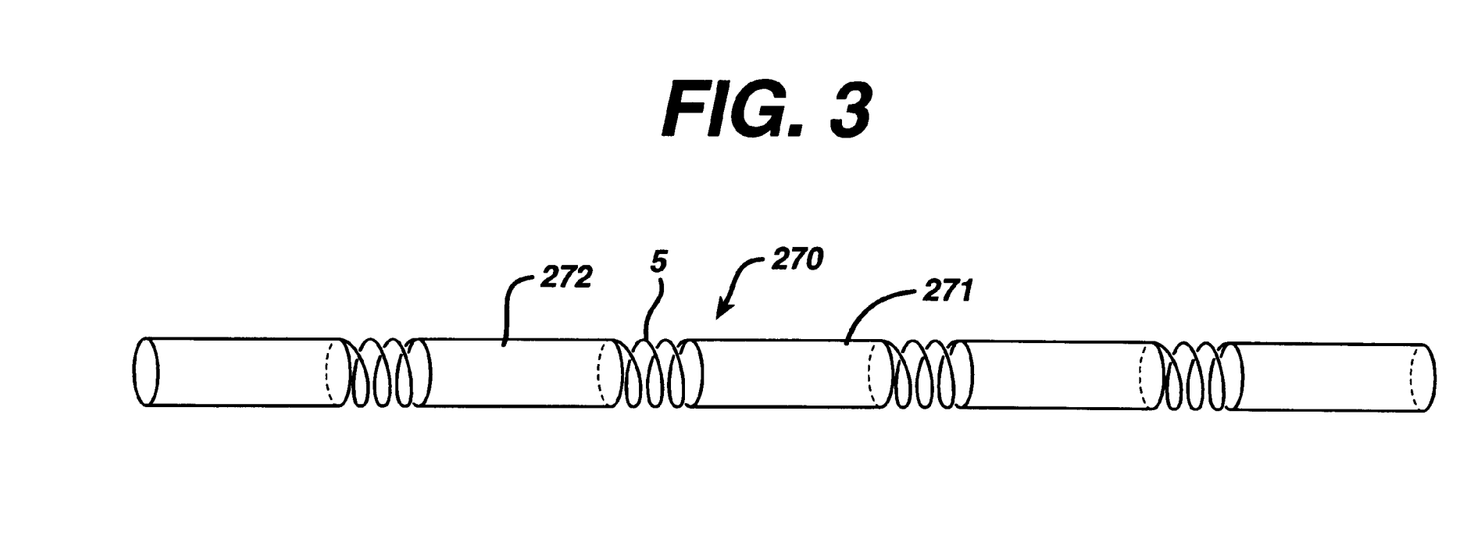
FIG. 3 is a schematic view of a second alternate embodiment stent of this invention.
Figure 6:
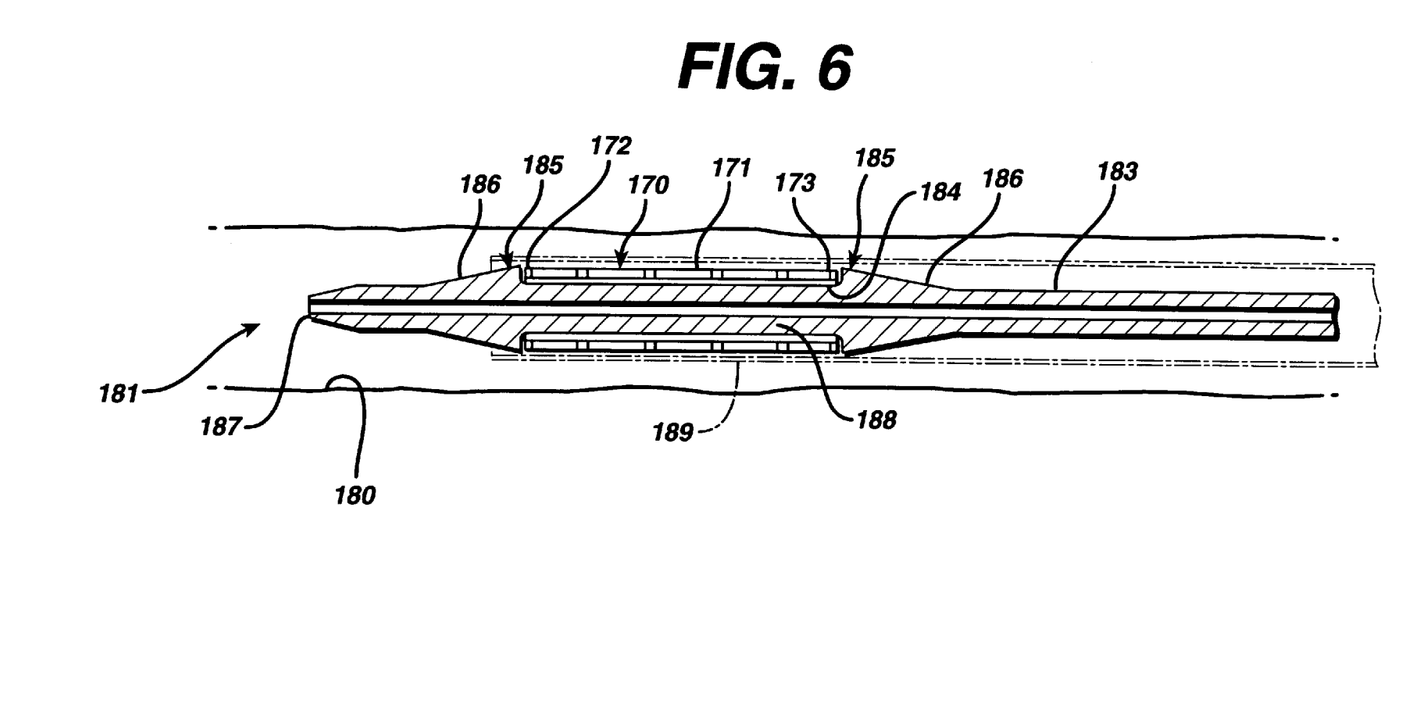
FIG. 6 is a stent of the invention loaded on a catheter.

The methods and apparatus of the present invention will be described in greater detail. Once again, it should be understood that the methods and apparatus of the present invention are useful not only for expanding the lumen of a body passageway, such as an artery, vein, or blood vessel of the human vascular system, but are also useful to perform the previously described procedures to intraluminally reinforce other body passageways or ducts, as previously described. As seen in FIG. 6, an expandable intraluminal vascular graft, or prosthesis, which may be of the type previously described in connection with FIGS. 1, 2, or 3 is disposed or mounted upon a catheter 183. Catheter 183 has an expandable, inflatable portion 184 associated therewith. Catheter 183 includes means for mounting and retaining 185 the expandable intraluminal vascular graft, or prosthesis, 170 on the expandable, inflatable portion 184 of catheter 183. Preferably, the mounting and retaining means 185 comprises retainer ring members 186 disposed on the catheter 183 adjacent the expandable inflatable portion 184 of catheter 183; and a retainer ring member 186 is disposed adjacent each end 172, 173 of the expandable intraluminal vascular graft, or prosthesis, 170.

As seen in FIG. 6, while retainer ring members are formed integral with catheter 183, and the retainer ring member 186 adjacent the leading tip 187 of catheter 183 slopes upwardly and away from catheter tip 187 in order to protect and retain graft or prosthesis, 170 as it is inserted into the lumen 181 of body passageway 180, as to be hereinafter described in greater detail. The remaining retainer ring member 186 as shown in FIG. 6, slopes downwardly away from tip 187 of catheter 183, to insure easy removal of catheter 183 from body passageway 180. After expandable intraluminal graft, or prosthesis, 170 has been disposed upon catheter 183, in the manner previously described, the graft, or prosthesis, 170 and catheter 183 are inserted within a body passageway 180 by catherization of the body passageway 180 in a conventional manner.

In a conventional manner, the catheter 183 and graft, or prosthesis, 170 are delivered to the desired location within the body passageway 180, whereat it is desired to expand the lumen 181 of body passageway 180 via intraluminal graft 170, or where it is desired to implant prosthesis 170. Fluoroscopy, and/or other conventional techniques may be utilized to insure that the catheter 183 and graft, or prosthesis, 170 are delivered to the desired location within the body passageway. Prosthesis, or graft, 170 are then expanded by expanding the expandable, inflatable portion 184 of catheter 183, whereby the prosthesis, or graft, 170 is forced radially, outwardly into contact with the body passageway 180. In this regard, the expandable, inflatable portion of catheter 183 may be a conventional angioplasty balloon 188. After the desired expansion of prosthesis, or graft, 170 has been accomplished, angioplasty balloon 188 may be removed in a conventional manner from body passageway 180. If desired, catheter 183, may be removed in a conventional manner from body passageway 180. If desired, catheter 183, having graft or prosthesis, 170 disposed thereon, may be initially encased in a convention Teflon™ sheath 189, which is pulled away from prosthesis, or graft, 170, prior to expansion of the prosthesis, or graft, 170.

It should be noted that the tubular shaped member 171 of prosthesis, or graft, 170 initially has the first predetermined, collapsed diameter d as described in connection with FIG. 1 in order to permit the insertion of the wire mesh tube, or tubular shaped member, 171 into the body passageway 180 as previously described. When it is desired to implant prosthesis 170 within a body passageway 180 for the purposes previously described, the wire mesh tube, or prosthesis 170, is expanded to the second diameter d' and the second, expanded diameter d' is variable and determined by the internal diameter of the body passageway 180. Accordingly, the expanded prosthesis 170, upon deflation of angioplasty balloon 188 will not be able to migrate from the desired location within the body passageway 180, nor will the expansion of the prosthesis 170 be likely to cause a rupture of the body passageway 180.

When it is desired to use expandable intraluminal graft 170 to expand the lumen 181 of a body passageway 180 having an area of stenosis, the expansion of intraluminal vascular graft 170 by angioplasty balloon 188, allows controlled dilation of the stenotic area and, at the same time controlled expansion of the vascular graft 170, whereby vascular graft 170 prevents the body passageway 180 from collapsing and decreasing the size of the expanded diameter d' of intraluminal vascular graft 170, as shown in FIG. 4, is variable and determined by the desired expanded internal diameter of body passageway 180. Thus, the expandable intraluminal graft 170 will not migrate away from the desired location within the body passageway 180 upon deflation of angioplasty balloon 188, nor will the expansion of intraluminal graft 170 likely cause a rupture of body passageway 180.

Because it is only necessary to inflate angioplasty balloon 188 one time in order to expand graft 170, it is believed that a greater amount of endothelium, or inner layer of the intima, or inner surface of the body passageway, will be preserved, insofar as the extent of endothelial denudation during transluminal angioplasty is proportional to the balloon inflation time. It is further believed that intact patches of endothelium between the elongate members of stent 170 may result in a rapid, multicentric endothelialization pattern as shown by experimental studies.

The stents of this invention are able to be made of polymeric or metallic materials, which in any event are expandable beyond their elastic limit. Furthermore, they can be made of shape memory materials such as nitinol and may have a certain shape memory imparted upon them also, as is disclosed in the art.

Stent 70, 170, 270 of the type previously described in connection with FIGS. 1, 2, and 3 are shown, and the tubular shaped members 71 of grafts, or prostheses, 170 have a biologically inert coating placed upon wall surfaces 74 of tubular shaped members 71. Examples of a suitable biologically inert coating would be porous polyurethane, Teflon™, or other conventional biologically inert plastic materials. The coating should be thin and highly elastic so as not to interfere with the desired expansion of the stent.

It is to be understood that the invention is not limited to the exact details of construction, operation, exact materials or embodiment shown and described, as obviously modifications and equivalents will be apparent to one skilled in the art. For example, the means for expanding the prosthesis or graft could be a plurality of hydraulically actuated rigid members disposed on a catheter, or a plurality of angioplasty balloons could be utilized by expand the prosthesis or graft. Accordingly, the invention is therefore to be limited only by the scope of the appended claims.

What is claimed is:

1. A stent comprising:
    at least two generally tubular segments, said segments formed from a plurality of interconnected struts each of said segments having a generally tubular shape with a circumference and a length; and
    a helical connector, said connector wound in the shape of a helix comprising at least one complete circumferential revolution about a circumference the size of a circumference of one of said segments, and said helical connector placed between said tubular segments.

2. The stent of claim 1 wherein said segments form a slotted tube.

3. The stent of claim 1 wherein said helix is made of wire.

4. The stent of claim 1 wherein said stent comprises a plurality of struts of generally curvilinear shape.

5. The stent of claim 1 sized to be useful in the coronary arteries.

6. The stent of claim 1 wherein said stent is balloon expandable.

7. The stent of claim 1 wherein said spiral connector is of a wave form.

8. The connector of stent of claim 7 wherein said spiral connector is generally linear in shape.

9. A pair of stents connected by a connecting member, said stents each having a generally tubular shape with a circumference and a length, said connecting member forming a spiral connector comprising at least one revolution about a circumference the size of a circumference of one of said stents, such that said spiral can be expanded both radially and circumferentially.

10. The stent of claim 9 wherein said stents is self-expanding.

11. The stent of claim 9 wherein said spiral connector is of a wave form.

12. The connector of stent of claim 11 wherein said spiral connector is generally linear in shape.

13. The stent of claim 9 wherein said stents form a slotted tube.

14. The stent of claim 9 wherein said spiral is made of wire.

15. The stent of claim 9 wherein one of said stents comprises a plurality of struts of generally curvilinear shape.

16. The stent of claim 9 sized to be useful in the coronary arteries.

17. The stent of claim 9 wherein one of said stents is balloon expandable.

18. The stent of claim 9 wherein one of said stents is self-expanding.

* * * * *